United States Patent
Brassil et al.

(10) Patent No.: US 6,186,783 B1
(45) Date of Patent: Feb. 13, 2001

(54) EVACUATION HAND PIECE FOR USE DURING DENTAL PROCEDURES

(75) Inventors: John Michael Brassil, Glenview; Shu Kun Chang, Evanston; Reynaldo Jose Quintana, Menlo Park; Dickon Isaacs, Chicago, all of IL (US)

(73) Assignee: Dentsply Research & Development Corp., Los Angeles, CA (US)

( * ) Notice: Under 35 U.S.C. 154(b), the term of this patent shall be extended for 0 days.

(21) Appl. No.: 08/953,108

(22) Filed: Oct. 17, 1997

(51) Int. Cl.[7] .................................................. A61C 17/06
(52) U.S. Cl. ................................................ 433/91; 433/96
(58) Field of Search .................................. 433/91, 92, 93, 433/94, 95, 96

(56) References Cited

U.S. PATENT DOCUMENTS

| | | | |
|---|---|---|---|
| 2,436,040 | * | 2/1948 | Friedman ................................ 433/91 |
| 2,637,106 | * | 5/1953 | Otis ........................................ 433/91 |
| 2,661,537 | | 12/1953 | Angell ..................................... 32/58 |
| 3,972,123 | | 8/1976 | Black ....................................... 32/58 |
| 4,340,366 | | 7/1982 | Heil ........................................ 433/82 |
| 4,412,402 | | 11/1983 | Gallant .................................... 51/439 |
| 4,482,322 | | 11/1984 | Hain et al. .............................. 433/88 |
| 4,487,582 | | 12/1984 | Warrin .................................... 435/8 |
| 4,492,575 | | 1/1985 | Mabille ................................... 433/88 |
| 4,733,503 | | 3/1988 | Gallant et al. .......................... 51/410 |
| 4,776,793 | * | 10/1988 | La Rocca ............................... 433/96 |
| 4,865,545 | * | 9/1989 | La Rocca ............................... 433/96 |
| 4,893,440 | | 1/1990 | Gallant et al. .......................... 51/436 |
| 5,145,367 | * | 9/1992 | Kasten ................................... 433/91 |
| 5,158,455 | | 10/1992 | Bailey .................................... 433/88 |
| 5,203,698 | | 4/1993 | Blake et al. ............................ 433/88 |
| 5,275,561 | | 1/1994 | Goldsmith ............................. 433/216 |
| 5,295,830 | * | 3/1994 | Shen et al. ............................. 433/91 |
| 5,330,354 | | 7/1994 | Gallant .................................... 433/88 |
| 5,334,016 | | 8/1994 | Goldsmith et al. .................... 433/29 |
| 5,334,019 | | 8/1994 | Goldsmith et al. .................... 433/88 |
| 5,350,299 | | 9/1994 | Gallant .................................... 433/88 |
| 5,525,058 | | 6/1996 | Gallant et al. .......................... 433/88 |
| 5,618,177 | | 4/1997 | Abbott .................................... 433/88 |

OTHER PUBLICATIONS

W.H. McGhee, et al, A Textbook of Operative Dentistry, 1956, pp. 266–273.
Bonner, Phillip, Air Abrasion: The New "Drill–Less" Dentistry, Dentistry Today, Sep. 1997 Issue, pp. 58–65.
Goldstein, Ronald, et al., Air–Abrasive Technology: Its New Role in Restorative Dentistry, JADA, vol. 15, May 1994, pp. 551–557.

* cited by examiner

Primary Examiner—John J. Wilson
(74) Attorney, Agent, or Firm—Douglas J. Hura; James B. Bieber

(57) ABSTRACT

An evacuation hand piece for collecting debris during dental procedures. The hand piece is adapted for attachment to evacuation apparatus and provides both intra- and extra-oral suction. A body member of the hand piece has a contoured outer gripping surface which makes the hand piece easier to grasp. A mask is disposed at one end of the hand piece to create a suction area which is larger than the cross sectional area of the body member. The mask is attached to a spherical tip of the body member to form a ball and socket-type connection which permits directional adjustment of the mask, thereby maximizing the effective extra-oral suction of the hand piece. The mask is formed from transparent material to allow viewing through the mask during dental procedures.

9 Claims, 3 Drawing Sheets

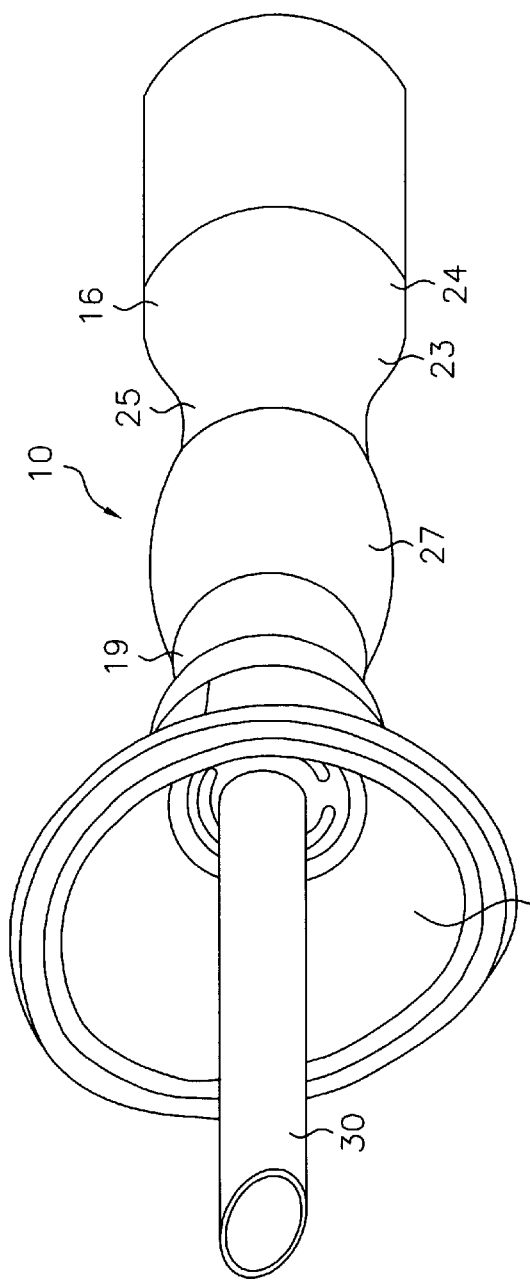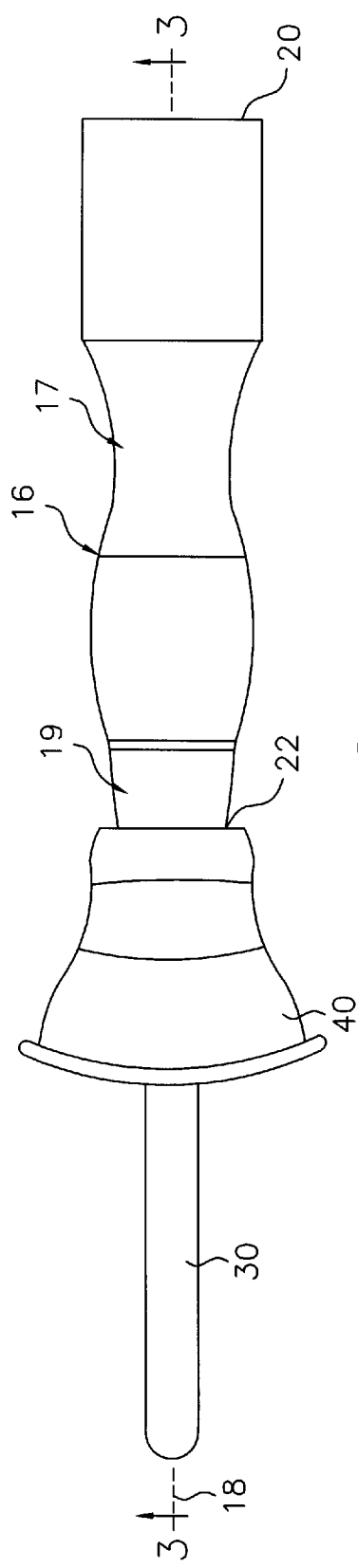

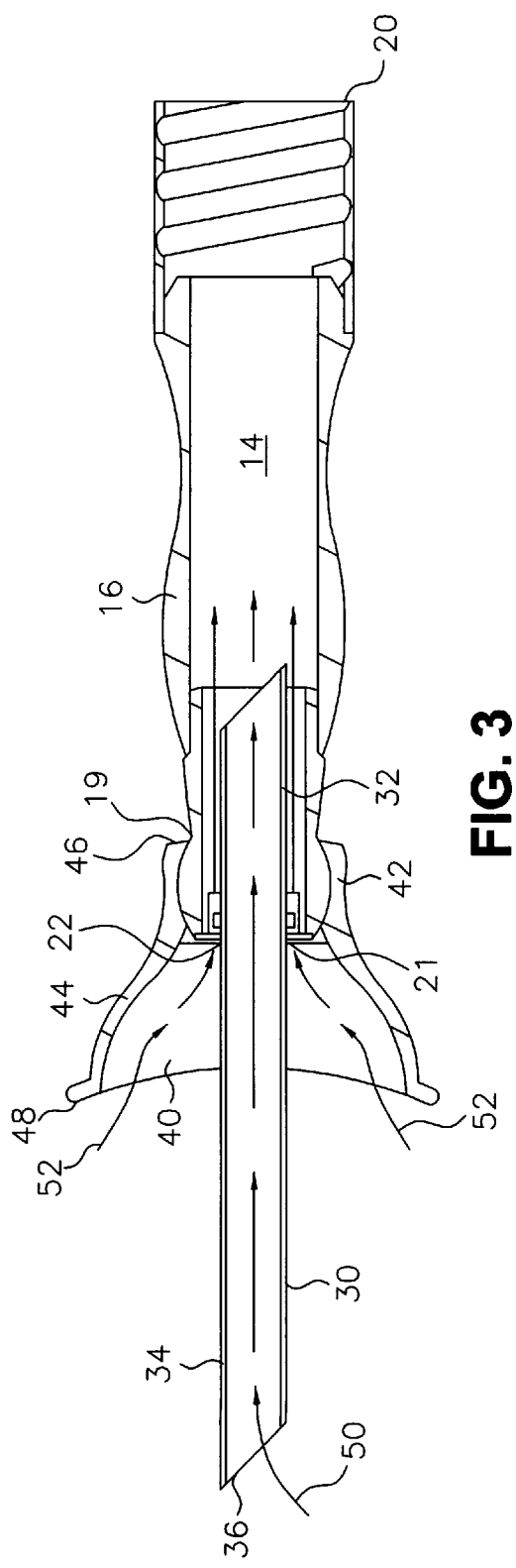
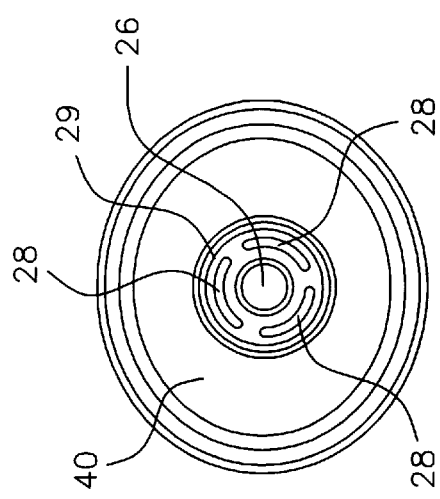
FIG. 3
FIG. 4

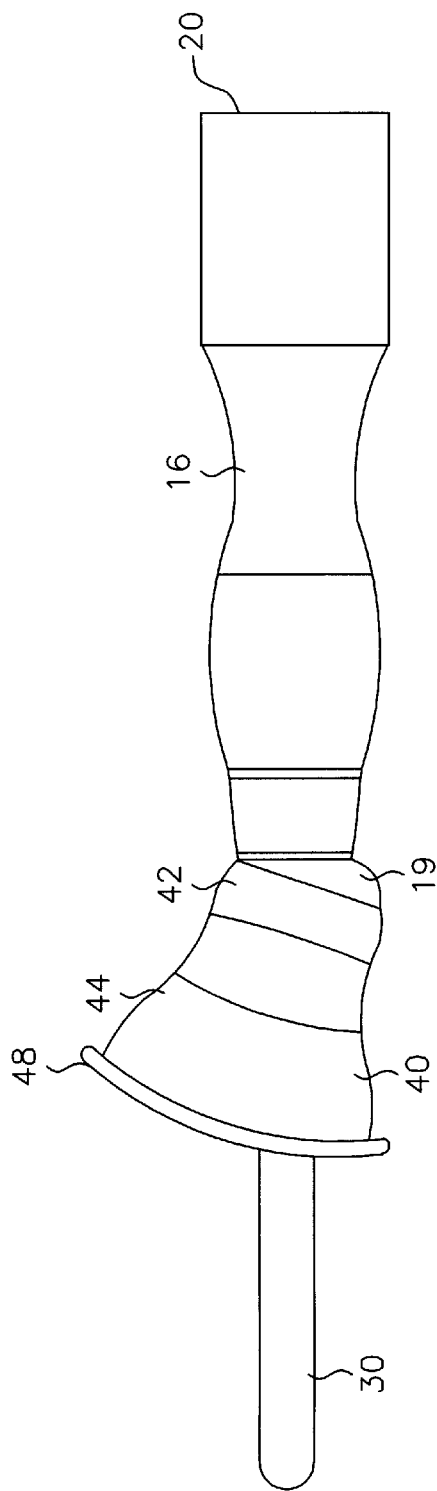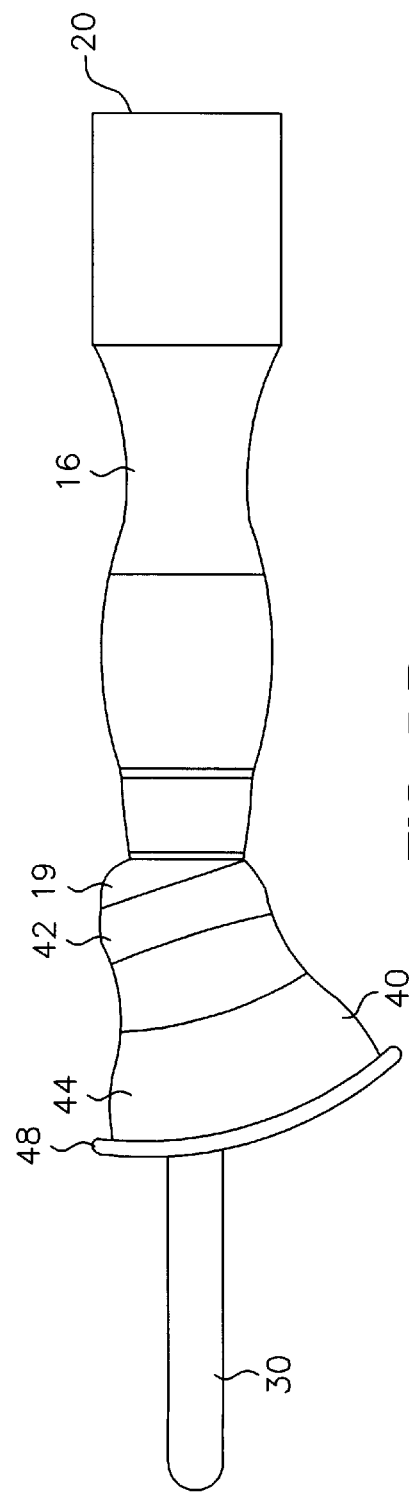

EVACUATION HAND PIECE FOR USE DURING DENTAL PROCEDURES

FIELD OF THE INVENTION

The present invention generally relates to dental apparatus, and more particularly relates to hand pieces for evacuating debris during dental procedures.

BACKGROUND OF THE INVENTION

Dental procedures, especially dental procedures using air abrasion systems, produce a number of particulate by-products which must be collected with evacuation apparatus. For example, when an air abrasion system is used to reduce a tooth, the process produces not only spent abrasive material but also portions of tooth, blood, gums, and other debris. This debris must be removed during the dental procedure to allow the dentist to monitor progress and to make the procedure more comfortable to the patient. During air abrasion procedures, it will be appreciated that while most of the abrasive material collects in the mouth of the patient, some abrasive material deflects out of the mouth and into the surrounding area. As a result, evacuation apparatus is needed which removes debris from both inside and outside the mouth.

Evacuation hand pieces are known which attempt to provide both intra- and extra-oral evacuation. These devices typically have a larger diameter cylindrical handle portion with a coaxially mounted smaller diameter tube. The tube is sized for insertion into the patient's mouth while the handle portion has holes extending through an end thereof and is generally positioned just outside of the mouth during dental procedures. These hand pieces are connected to evacuation means such as a vacuum pump to create a suction flow through the hand piece. Accordingly, suction flow is created through the tube and the holes located in the handle portion.

Unfortunately, conventional evacuation hand pieces do not adequately collect debris from both inside and outside the mouth. The area of suction created outside the mouth in such hand pieces is limited by the size of the handle portion. The handle portion must be small enough to be held and also must be small enough to allow the dentist to adequately see inside the mouth during the procedure. It will be appreciated, however, that the extra-oral suction area created by the hand piece is directly related to the size of the handle portion, and therefore a smaller diameter handle portion evacuates a smaller extra-oral area. Accordingly, conventional evacuation hand pieces are either too big and therefore cannot be easily held or used during dental procedures, or are too small and collect only a fraction of the debris which deflects from the mouth.

Conventional evacuation hand pieces further fail to maximize extra-oral suction from all areas of the mouth. During some procedures, the evacuation hand piece must be placed near the corner of the mouth and therefore a portion of the holes in the handle portion are disposed near the cheek of the patient rather than the mouth. Debris, however, deflects out of the mouth and therefore the holes disposed over the cheek are ineffective to collect debris. Accordingly, conventional evacuation hand pieces do not maximize the effectiveness of the extra-oral suction holes.

Furthermore, the extra-oral suction provided by conventional evacuation hand pieces is localized in that it does not address debris escaping from the other side of the mouth. During a dental procedure, the evacuation hand piece is typically placed on a first side of the mouth while the dentist works on a second side. As noted above, a handle with holes is typically provided in conventional hand pieces for creating extra-oral suction. The suction produced by such hand pieces, however, simply collects debris from the first side of the mouth. As a result, debris escapes through the second side of the mouth unimpeded by the conventional hand piece.

Furthermore, conventional evacuation hand pieces are overly cumbersome to sterilize between patients. During dental procedures, the evacuation hand piece is positioned so that the smaller tube extends into the patient's mouth while the handle is located near the patient's mouth. Conventional hand pieces have an integral tube and handle assembly and therefore both the tube and handle must be sterilized between each use.

SUMMARY OF THE INVENTION

A general aim of the present invention is to provide an evacuation hand piece which is compact yet provides superior intra- and extra-oral evacuation.

A more detailed object of the present invention is to provide an evacuation hand piece which maximizes extra-oral suction capacity.

It is also an object of the prevention to provide an evacuation hand piece which performs extra-oral evacuation on an area which is larger the body of the hand piece yet still allows the dentist to view the procedure.

In light of the above, the present invention provides an evacuation hand piece which produces improved intra- and extra-oral evacuation. The evacuation hand piece includes a body member having attachment and suction ends. The suction end of the body member carries a flange having a center orifice and outer orifices. An intra-oral tube is mounted through the center orifice and extends from the suction end for insertion inside the mouth. A mask is attached to the suction end for directing the extra-oral suction through the outer orifices. The mask has an open end which is larger than the body member for increasing the extra-oral suction area.

In accordance with the present invention, the mask is pivotable to adjust the direction of the extra-oral suction. The suction end of the body member has a spherical shape and the mask has an attachment end which closely conforms to the spherical shape to form a ball and socket-type connection between the suction end and the attachment end. As a result, the mask may be redirected as necessary to optimize the direction of the extra-oral suction flow. The mask is made from a flexible material so that it closely engages the face of the patient. In this position, the extra-oral suction flow of the hand piece creates an inflow through the open side of the patient's mouth, thereby preventing debris from escaping through that side.

These and other aims, objectives, and advantages of the invention will become more apparent from the following detailed description when taken in conjunction with the accompanying drawings.

BRIEF DESCRIPTION OF THE DRAWINGS

FIG. 1 is a perspective view of an evacuation hand piece in accordance with the present invention.

FIG. 2 is a side view of the evacuation hand piece shown in FIG. 1.

FIG. 3 is a full sectional view of the evacuation hand piece taken along line 3—3 of FIG. 2.

FIG. 4 is an end view of the evacuation hand piece of FIG. 1.

FIGS. 5A and 5B are side views of the evacuation hand piece of FIG. 1 with the mask redirected up and down, respectively.

While the invention is susceptible of various modifications and alternative constructions, certain illustrative embodiments thereof have been shown in the drawings and will be described below in detail. It should be understood, however, that there is no intention to limit the invention to the specific forms disclosed, but on the contrary, the invention is to cover all modifications, alternative constructions and equivalents falling within the spirit and scope of the invention as defined by the appended claims.

DETAILED DESCRIPTION OF THE PREFERRED EMBODIMENT

Referring now to the drawings, FIG. 1 shows an evacuation hand piece 10 for attachment to a hose leading to evacuation apparatus (not shown). The evacuation hand piece 10 is used to create suction flow for collecting particulates such as abrasive material, portions of tooth, saliva, and blood, from a patient's mouth during dental procedures performed with an air abrasion system. The evacuation hand piece 10 is positioned adjacent the mouth of the patient to perform both intra- and extra-oral evacuation.

In greater detail, the evacuation hand piece 10 comprises a body member 16 having a generally cylindrical shape extending along an axis 18 (FIG. 2). The body member 16 has a connection end 20 adapted for attachment to the hose 12 and a suction end 22 which is positioned near the mouth of the patient during dental procedures. The body member generally has a handle portion 17 located nearer the connection end 20 and a tip portion 19 located nearer the suction end 22. As best shown in FIG. 3, a central passage 14 extends through the body member 16 from the connection end 20 to the suction end 22. A suction flange 21 is formed at the suction end 22 which defines the intra- and extra-oral suction flow paths, as described in greater detail below.

In accordance with certain aspects of the present invention, the body member 16 has a contoured outer gripping surface 24 which enables the hand piece 10 to be more easily held. As best shown in FIG. 1, the body member 16 has a flared portion 23 near the connection end 20 which gradually slopes to a smaller diameter neck portion 25. The neck portion 25 transitions into a bulge portion 27, the diameter of which is smaller near the neck portion 25, gradually increases to a larger diameter, and then gradually decreases again to a smaller diameter near the tip portion 19. The contoured shape of the flared, neck, and bulge portions 23, 25, 27 give the outer gripping surface 24 a shape that more closely conforms to the hand. As a result, the evacuation hand piece 10 is more comfortable to hold and does not slip out of the hand as easily as conventional, uniform diameter evacuation hand pieces.

The suction flange 21 has a center orifice 26 and a plurality of outer orifices 28 for allowing intra- and extra-oral suction, respectively. As best shown in FIG. 4, the center orifice 26 is centered substantially on the axis 18 of the body member 16 and has a predetermined diameter, as described more fully below. The outer orifices 28 are located radially about the axis between the outer edge of the center orifice 26 and a periphery 29 of the suction flange 21. The outer orifices 28 are formed as arcuate slots, however other shapes may be used for the outer orifices in accordance with the present invention. Both the center orifice 26 and the outer orifices 28 extend completely through the suction flange 21 to communicate with the central passage 14 of the body member 16.

The hand piece 10 has an intra-oral tube 30 for directing suction inside the mouth. As best shown in FIG. 2, the intra-oral tube 30 is mounted through the center orifice 26 of the suction flange 21 so that the tube is substantially coaxial with the body member 16. The intra-oral tube 30 has a base portion 32 disposed inside the body member 16 and a tip portion 34 extending outside the body member for insertion into the mouth during dental procedures (FIG. 3). The end of the tip portion 34 of the intra-oral tube 30 has a suction opening 36 through which intra-oral suction flows.

The intra-oral tube 30 is hollow to create a suction flow which travels through the suction opening 36 and tube 30 into the central passage 14. The intra-oral tube 30 is cylindrical and the diameter of the center orifice 26 is sized slightly smaller than an outer diameter 38 of the intra-oral tube 30 so that the tube frictionally yet slidingly engages the center orifice. The intra-oral tube 30 is preferably formed of a resilient material so that the tube is adjustable with respect to the body member 16 but is also frictionally held in place after repositioning. In the most preferred embodiment, the intra-oral tube 30 is a disposable high-vacuum evacuation (or HVE) tip and therefore is simply replaced, rather than sterilized, between patients.

A mask 40 is attached to the body member near the suction end 22 for expanding the extra-oral suction of the hand piece 10. The mask 40 has an attachment portion 42 which overlies part of the suction end 22 of the body portion 16. In the preferred embodiment, the mask 40 is a made of a flexible material so that the attachment portion 42 resiliently conforms to the tip portion 19 of the body member 16. The mask 40 has a sidewall 44 extending from the attachment portion 42 away from the suction end 22 of the body member 16. The sidewall 44 has a generally frusto-conical shape with attachment and open ends 46, 48. The attachment end 46 is located near and has substantially the same diameter as the attachment portion 42. The open end 48 is spaced from the attachment portion 42 and has a cross-sectional area which is greater than that of the attachment end 46. When attached to the body member 16, the mask 40 is positioned so that the open end 48 is spaced from the suction end 22 of the body member 16. It will be appreciated that while the mask 40 of the illustrated embodiment has a frusto-concial shape, other shapes may be used in accordance with the present invention as long as the open end 48 of the sidewall has a larger cross sectional area than the attachment end 46. In the preferred embodiment, the mask 40 is formed from material that is transparent, to allow the dentist to see through the mask to observe the mouth during dental procedures, and flexible, to allow the mask to closely and comfortably engage with the patient's face.

In accordance with significant aspects of the present invention, the tip portion 16 of the body member 16 has spherical shape for allowing directional adjustment of the mask 40. As best shown in FIG. 3, the tip portion 19 of the body member 16 resembles a ball while the attachment portion 42 of the mask 40 generally conforms to the spherical shape. The suction end 22 and attachment portion 42 form a ball and socket-type connection so that the position of the mask 40 on the body member 16 may be adjusted in different directions. FIGS. 5A and 5B illustrate the mask rotated in a fully upward and fully downward position, respectively. The adjustment of the mask 40 allows the hand piece 10 to maximize extra-oral suction since the suction area of the mask 40 may be pointed in the optimal direction.

In operation, the hand piece 10 is connected to evacuation apparatus to create a suction flow through the hand piece. Intra-oral suction (represented by arrows 50 in FIG. 3) is directed inside the mouth and flows through the suction opening 36, intra-oral tube 30, and central passage 14. Extra-oral suction (represented by arrows 52 in FIG. 3) initiates outside the mouth and has a suction area roughly equal to the cross-sectional area of the open end 48 of the mask 40. Extra-oral suction 52 flows through the mask 40, outer orifices 28 and central passage 14. Both the intra- and extra-oral suction continues from the central passage 14 through the hose to ultimately reach the evacuation apparatus. The adjustable positioning of the intra-oral tube 30 with respect to the body member 16 allows the intra- and extra-oral suction to be adjusted relative to one another. The adjustment allows the hand piece 10 to be adapted for different procedures and different sized mouths.

It will be appreciated that the mask 40 not only evacuates the side of the mouth at which the mask is located but also reduces the amount of debris escaping the opposite side of the mouth. During a dental procedure, the mask 40 is typically placed adjacent a first side of the patient's mouth while the dentist works on a second or open side of the patient's mouth. When the mask 40 of resilient material is placed in contact with the first side of the mouth and the evacuation hand piece 10 is connected to evacuation apparatus, a suction flow is created which collects debris from the first side of the mouth. The suction flow, however, also creates an inflow of air through the open side of the mouth which prevents debris from escaping through that side of the mouth, thereby reducing the amount of mess generated during the dental procedure.

From the foregoing, it will be apparent that the present invention brings to the art an evacuation hand piece with improved intra- and extra-oral suction. The hand piece has contoured outer surface which conforms to the hand of the dentist. Furthermore, the hand piece has a mask which increases the extra-oral suction area and creates an inflow through the open side of the mouth. The mask and body member form a ball and socket connection which allows the mask to be rotated in a number of different directions, thereby maximizing the effectiveness of the extra-oral suction. The evacuation hand piece further uses standard, disposable HVE tips for the inter-oral evacuation, thereby facilitating quicker sterilization of the hand piece between patients.

What is claimed is:

1. An evacuation hand piece adapted for connection to evacuation apparatus for collecting debris during dental procedures, the evacuation hand piece comprising:

an elongate body member extending along an axis and having connection and suction ends, a central passage extending through the body member from the connection end to the suction end, a suction flange located at the suction end including a center orifice of a given diameter centered about the axis and a plurality of outer orifices located between the center orifice and a periphery of the suction flange, the center orifice and outer orifices extending through the suction flange to fluidly communicate with the central passage;

a hollow and elongated intra-oral tube slidably and adjustably mounted through the center orifice and having a tip end extending past the suction end of the body member, the intra-oral tube having an outside diameter sized to frictionally yet slidably engage the given diameter of the center orifice; and a mask attached to and extending from the suction end of the body member, the mask having a sidewall with attachment end disposed near the suction end of the body member and an open end spaced from the attachment end, the open end having a larger cross-sectional area than the attachment end.

2. The evacuation hand piece of claim 1 wherein the suction end has a generally spherical shape, and the mask has a neck portion attached to the sidewall having an inner surface which generally conforms to the spherical shape of the suction end, the suction end and attachment portion forming a ball and socket connection which allows the mask to be adjusted in different directions.

3. The evacuation hand piece of claim 1 in which the intra-oral tube is a disposable HVE tip.

4. The evacuation hand piece of claim 1 in which the body member has an outer gripping surface located near the connection end, the outer gripping surface including a flared portion of a first larger diameter sloping to a neck portion of a smaller diameter, the neck portion transitioning to a bulge portion of a second larger diameter.

5. The evacuation hand piece of claim 1 in which the outer orifices are disposed radially about the axis.

6. The evacuation hand piece of claim 5 in which the outer orifices are formed as arcuate slots.

7. The evacuation hand piece of claim 1 in which the mask is formed from transparent material.

8. An evacuation hand piece adapted for connection to evacuation apparatus for reducing stray debris during a dental procedure, the evacuation hand piece being positioned adjacent a face of a patient to collect debris from inside and an area surrounding a first side of a mouth of the patient while the dental procedure is performed on a second side of the mouth, the evacuation hand piece comprising:

an elongate body member extending along an axis and having connection and suction ends, a central passage extending through the body member from the connection end to the suction end, a suction flange located at the suction end including a center orifice of a given diameter centered about the axis and a plurality of outer orifices located between the center orifice and a periphery of the suction flange, the center orifice and outer orifices extending through the suction flange to fluidly communicate with the central passage;

a hollow and elongated intra-oral tube slidably and adjustably mounted through the center orifice and having a tip end extending past the suction end of the body member, the intra-oral tube having an outside diameter sized to frictionally yet slidably engage the given diameter of the center orifice; and a mask attached to and extending from the suction end of the body member, the mask having a sidewall with attachment end disposed near the suction end of the body member and an open end spaced from the attachment end, wherein the mask is formed from resilient material so that, when the open end is positioned to engage the first side of the mouth, an inflow is created through the second side of the mouth.

9. An evacuation hand piece adapted for connection to evacuation apparatus for collecting debris during dental procedures, the evacuation hand piece comprising:

an elongate body member extending along an axis and having connection and suction ends, a central passage extending through the body member from the connection end to the suction end, a suction flange located at the suction end including a center orifice of a given diameter centered about the axis and a plurality of outer orifices located between the center orifice and a periphery of the suction flange, the center orifice and outer orifices extending through the suction flange to fluidly communicate with the central passage;

a hollow and elongated intra-oral tube slideably mounted through the center orifice and having a tip end extending past the suction end of the body member, the intra-oral tube having an outside diameter sized to frictionally yet slidably engage the given diameter of the center orifice; and a mask attached to hand extending from the suction end of the body member, the mask having a sidewall with attachment end disposed near the suction end of the body member and an open end spaced from the attachment end, the open end having a larger cross-sectional area than the attachment end, wherein the suction end has a generally spherical shape, and the mask has a neck portion attached to the sidewall having an inner surface which generally conforms to the spherical shape of the suction end, the suction end and attachment portion forming a ball and socket connection which allows the mask to be adjusted in different directions.

* * * * *